(12) United States Patent
Sheth et al.

(10) Patent No.: US 7,076,290 B2
(45) Date of Patent: Jul. 11, 2006

(54) METHOD AND APPARATUS FOR DETECTING AND DISCRIMINATING ARRHYTHMIAS

(75) Inventors: Nirav V. Sheth, Coon Rapids, MN (US); Eduardo N. Warman, Maple Grove, MN (US); Michael F. Hess, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 289 days.

(21) Appl. No.: 10/682,982

(22) Filed: Oct. 10, 2003

(65) Prior Publication Data

US 2005/0080347 A1    Apr. 14, 2005

(51) Int. Cl.
    *A61B 5/04* (2006.01)
(52) U.S. Cl. .................................... 600/515
(58) Field of Classification Search ............. 607/4, 607/5, 9; 600/515–619
    See application file for complete search history.

(56) References Cited

U.S. PATENT DOCUMENTS

| | | | |
|---|---|---|---|
| 4,316,472 A | 2/1982 | Mirowski et al. | |
| 4,375,817 A | 3/1983 | Engle et al. | |
| 4,577,633 A | 3/1986 | Berkovits et al. | |
| 4,587,970 A | 5/1986 | Holley et al. | |
| 4,726,380 A | 2/1988 | Vollmann et al. | |
| 4,727,877 A | 3/1988 | Kallok | |
| 4,830,006 A | 5/1989 | Haluska et al. | |
| 4,880,005 A | 11/1989 | Pless et al. | |
| 4,949,719 A | 8/1990 | Pless et al. | |
| 5,107,850 A | 4/1992 | Olive | |
| 5,117,824 A | 6/1992 | Keimel et al. | |
| 5,163,427 A | 11/1992 | Keimel | |
| 5,183,040 A * | 2/1993 | Nappholz et al. | 607/4 |
| 5,188,105 A | 2/1993 | Keimel | |
| 5,284,491 A | 2/1994 | Sutton et al. | 607/17 |
| 5,411,524 A | 5/1995 | Rahul | |
| 5,545,186 A | 8/1996 | Olson et al. | |
| 5,968,079 A | 10/1999 | Warman et al. | 607/5 |
| 6,091,988 A | 7/2000 | Warman et al. | |
| 6,477,420 B1 | 11/2002 | Struble et al. | 607/14 |

FOREIGN PATENT DOCUMENTS

WO    EP 0 870 519 B1    2/2004

OTHER PUBLICATIONS

U.S. Appl. No. 10/292,285.

* cited by examiner

*Primary Examiner*—George Manuel
(74) *Attorney, Agent, or Firm*—Michael C. Soldner; Girma Wolde-Michael (57) ABSTRACT

An apparatus and method for discriminating arrhythmias that includes sensing a heart rate indicative of an arrhythmia associated with a first portion of a heart, determining regularity of the sensed heart rate, determining an event interval variability associated with a second portion of the heart, and classifying the arrhythmia in response to the determined event interval variability.

16 Claims, 3 Drawing Sheets

METHOD AND APPARATUS FOR DETECTING AND DISCRIMINATING ARRHYTHMIAS

FIELD OF THE INVENTION

The present invention relates generally to implantable medical devices, and particularly to a device and method for detecting and discriminating between an arrhythmia associated with one portion of the heart using rhythm information.

BACKGROUND OF THE INVENTION

In the past, atrial arrhythmias have been largely undertreated due to the perception that these arrhythmias are relatively benign. As more serious consequences of persistent atrial fibrillation have come to be understood, such as an associated risk of relatively more serious ventricular arrhythmias and stroke, there is a greater interest in providing implantable atrial or dual chamber cardioverter defibrillators for treating atrial arrhythmias.

Atrial fibrillation (AF) is generally treatable with relatively high voltage defibrillation shocks, which are generally painful to the patient, or with less painful high frequency pulse bursts. Atrial flutter (AFL) can be treated by antitachycardia pacing therapies, pulse bursts or cardioversion shocks. Reliable discrimination between atrial flutter and atrial fibrillation is important in selecting the appropriate atrial arrhythmia therapy and is also useful in monitoring a patient's arrhythmia disease status, managing medical therapy, and evaluating the effectiveness of arrhythmia therapies.

In atrial flutter, the atria beat at an elevated rate that is highly regular, typically at 200 to 320 beats per minute. The ventricles are unable to respond to each atrial depolarization so a partial block of atrioventricular conduction is usually present causing the ventricles to beat synchronously with every other or every third atrial depolarization. Thus the ventricular heart rate can be in a normal range or elevated during atrial flutter but is typically regular. In atrial fibrillation, the atria depolarize at an elevated rate that is typically irregular. However, atrial fibrillation can occur at regular rates in some patients. Atrial depolarizations are conducted to the ventricles intermittently, causing an irregular ventricular rate. The ventricular rate can be in a normal range or elevated during atrial fibrillation.

Early arrhythmia detection systems for automatic cardioverter/defibrillators relied upon the presence or absence of electrical or mechanical heart activity and/or the rate of the cardiac electrogram to detect ventricular tachycardia or fibrillation. Rate or interval ranges that characterize a tachycardia as opposed to fibrillation could be specified for detecting and discriminating tachycardia and fibrillation. However, tachycardia and fibrillation may have similar or overlapping rates, making it difficult to distinguish high rate tachycardia from fibrillation. Furthermore, since some rapid ventricular rhythms are due to activity that originates in the atria, it has become apparent that evaluation of the ventricular rhythm alone was not adequate in classifying the rhythm or selecting an appropriate arrhythmia therapy.

Methods for improving the specificity of ventricular tachycardia detection and for discriminating ventricular tachycardias from supra-ventricular tachycardias have been employed or proposed for use in commercial dual chamber cardioverter defibrillators. Such methods may include measurements of suddenness of onset, rate variability, waveform morphology, and/or the order and timing of atrial and ventricular events. For example, a method for classifying cardiac arrhythmias by examining the atrial and ventricular activity of the heart is generally disclosed in U.S. Pat. No. 5,107,850 issued to Olive, wherein the regularity and value of the ventricular rate, atrial rate and the atrial-ventricular interval are used for discriminating between atrial rhythms and ventricular rhythms. An arrhythmia detection and classification system that employs a prioritized set of inter-related rules for arrhythmia detection is generally disclosed in U.S. Pat. No. 5,545,186 issued to Olson et al.

Methods for specifically classifying atrial arrhythmias, however, remain dependent on atrial rate information without regard to the ventricular rhythm in current commercially available devices. Such information may include the atrial rate and the regularity of the atrial rate. A range of atrial rates may be specified for detecting atrial flutter and a different, generally higher, range of atrial rates may be specified for detecting atrial fibrillation. However, because the atrial rate could be the same during atrial flutter and atrial fibrillation, specified ranges for atrial flutter and atrial defibrillation detection may overlap and therefore rate information alone is not always adequate for detecting and discriminating atrial flutter and atrial fibrillation. When an atrial rate is detected in this overlap range, atrial cycle length regularity may be used for discriminating between atrial flutter and atrial fibrillation, for example.

Methods for detecting and discriminating atrial fibrillation and atrial flutter using discriminatory signatures of the ventricular cycle lengths displayed in a scatter plot are generally disclosed in U.S. patent application Ser. No. 10/292,285, incorporated herein by reference in its entirety.

BRIEF DESCRIPTION OF THE DRAWINGS

Advantages and features of the present invention will be readily appreciated as the same becomes better understood by reference to the following detailed description when considered in connection with the accompanying drawings, in which like reference numerals designate like parts throughout the figures thereof and wherein.

DETAILED DESCRIPTION OF THE INVENTION

Dual chamber cardioverting and defibrillating devices sense both atrial and ventricular events for the detection of arrhythmias in both atrial and ventricular chambers. The present invention takes advantage of the ability to monitor the ventricular rhythm in such implantable medical devices upon detecting a high atrial rate for detecting and classifying atrial arrhythmias. As such, the present invention is preferably embodied in a dual chamber or multichamber cardiac stimulation device capable of sensing atrial and ventricular electrogram signals and delivering atrial arrhythmia therapies according to the type of atrial arrhythmia detected. Atrial arrhythmia therapies may include anti-tachycardia pacing, high frequency pulse bursts, and/or higher voltage cardioversion and/or defibrillation pulses. The cardiac stimulation device may additionally be capable of delivering ventricular arrhythmia therapies and may provide bradycardia pacing or other types of cardiac stimulation therapies. However, it is recognized that the delivery of arrhythmia therapies is not necessary for practicing the invention and that aspects of the present invention for detecting and classifying atrial arrhythmias may be implemented in a cardiac monitoring device.

The present invention provides a method for discriminating atrial flutter from atrial fibrillation, which utilizes atrial and ventricular rhythm information. The present invention may be usefully practiced in an implantable cardiac stimulation device capable of sensing cardiac activity for detecting arrhythmias and delivering cardiac stimulation pulses for treating detected arrhythmias. Aspects of the present invention may alternatively be employed in internal or external cardiac monitoring devices used for detecting arrhythmias.

The atrial flutter/atrial fibrillation discrimination method involves applying multiple atrial arrhythmia detection criteria based on atrial rate, atrial cycle length regularity, ventricular cycle length regularity and/or ventricular cycle length determined from sensed atrial and ventricular electrogram signals or other cardiac-related signals from which atrial and ventricular rates may be derived. The method examines the intrinsic ventricular rhythm when a sensed atrial rate exceeds a selectable minimum atrial arrhythmia detection rate and is lower than a selectable rate that would clearly indicate atrial fibrillation, and the atrial rate is regular such that atrial flutter and atrial fibrillation cannot be reliably distinguished. If ventricular pacing is present and the patient is not pacemaker dependent, ventricular pacing is inhibited to allow the intrinsic ventricular rate to be sensed. Ventricular pacing inhibition may be achieved by reducing the ventricular pacing rate to a rate lower than the intrinsic ventricular rate.

Atrial flutter is distinguished from atrial fibrillation by regular ventricular cycle lengths or ventricular cycle lengths that correspond to a multiple of the atrial cycle length indicating, for example, 1:1, 2:1 or 3:1 conduction of atrial flutter waves to the ventricles. In addition, a pattern of ventricular and atrial cycle lengths typifying Wenckebach conduction can be used to identify atrial flutter. Atrial fibrillation is distinguished from atrial flutter by irregular ventricular cycle lengths showing no correspondence to atrial cycle lengths.

The atrial flutter or atrial fibrillation classification of the atrial rhythm may be used for selecting or managing an appropriate atrial arrhythmia therapy, evaluating therapy effectiveness, and/or monitoring a patient's arrhythmia status.

Figure 1:
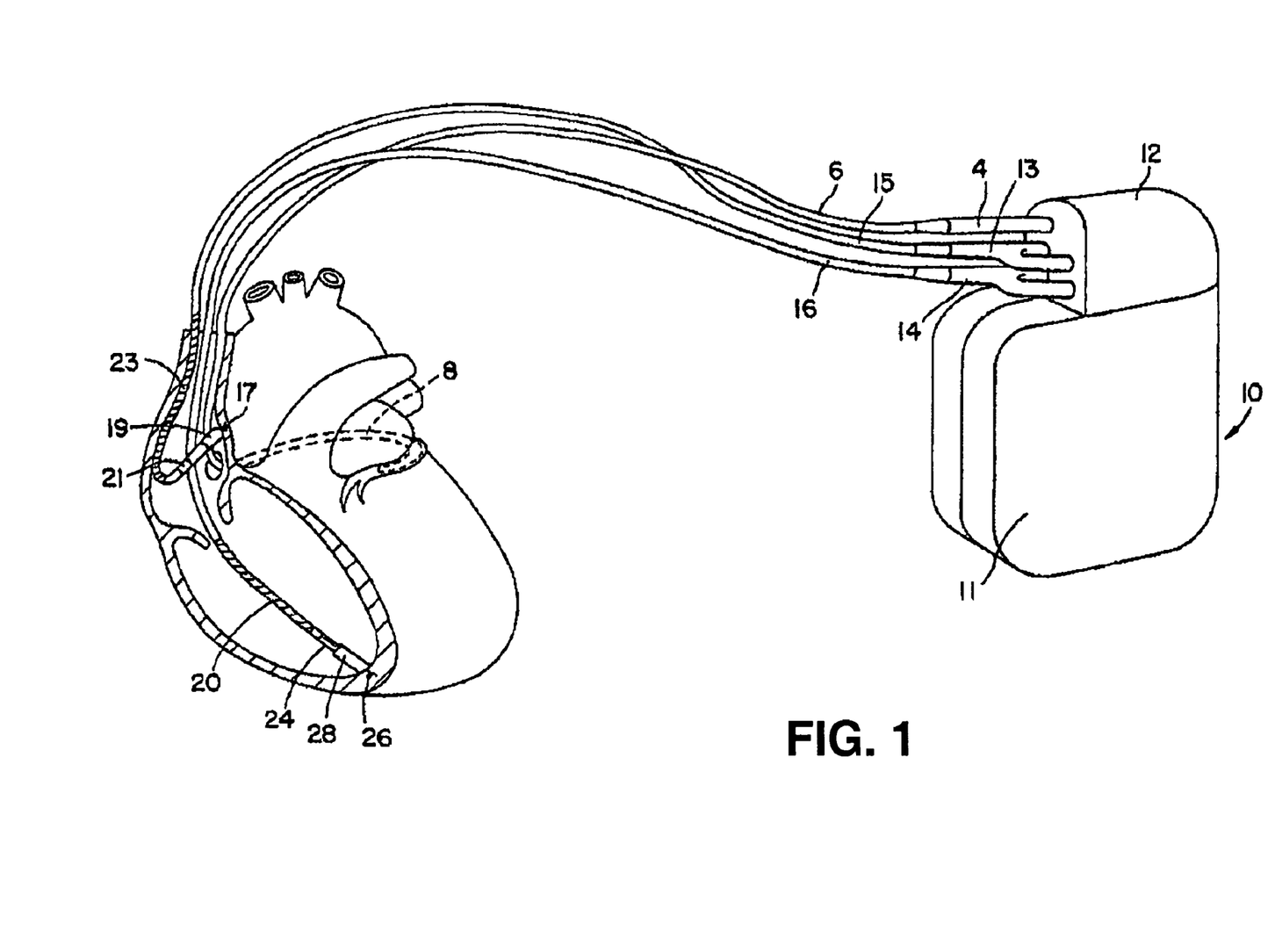
FIG. 1 is a schematic diagram of an exemplary implantable medical device in which the present invention may be practiced.

FIG. 1 is a schematic diagram of an exemplary implantable medical device in which the present invention may be practiced. As illustrated in FIG. 1, an implantable medical device 10 according to the present invention is provided with multi-chamber pacemaking, cardioversion, and defibrillation capabilities and is coupled to a patient's heart by way of three leads 6, 15, and 16. A connector block 12 receives the proximal end of a right ventricular lead 16, a right atrial lead 15 and a coronary sinus lead 6, used for positioning electrodes for sensing and stimulation in three or four heart chambers. In FIG. 1, the right ventricular lead 16 is positioned such that its distal end is in the right ventricle (RV) for sensing right ventricular cardiac signals and delivering pacing or shocking pulses in the right ventricle. For these purposes, right ventricular lead 16 is equipped with a ring electrode 24, a tip electrode 26, optionally mounted retractably within an electrode head 28, and RV coil electrode 20, each of which are connected to an insulated conductor contained within the body of lead 16. The proximal end of the insulated conductors are coupled to corresponding connectors carried by bifurcated connector 14 at the proximal end of lead 16 for providing electrical connection to the device 10, referred to hereafter as "implantable cardioverter defibrillator" or "ICD".

The right atrial lead 15 is positioned such that its distal end is in the vicinity of the right atrium and the superior vena cava (SVC). Lead 15 is equipped with a ring electrode 21 and a tip electrode 17, optionally mounted retractably within electrode head 19, for sensing and pacing in the right atrium. Lead 15 is further equipped with an SVC coil electrode 23 for delivering high-energy shock therapy. The ring electrode 21, the tip electrode 17 and the SVC coil electrode 23 are each connected to an insulated conductor with the body of the right atrial lead 15. Each insulated conductor is coupled at its proximal end to a connector carried by bifurcated connector 13.

The coronary sinus lead 6 is advanced within the vasculature of the left side of the heart via the coronary sinus and great cardiac vein. The coronary sinus lead 6 is shown in the embodiment of FIG. 1 as having a defibrillation coil electrode 8 that may be used in combination with either the RV coil electrode 20 or the SVC coil electrode 23 for delivering electrical shocks for cardioversion and defibrillation therapies. In other embodiments, coronary sinus lead 6 may also be equipped with a distal tip electrode and ring electrode for pacing and sensing functions in the left chambers of the heart. The coil electrode 8 is coupled to an insulated conductor within the body of lead 6, which provides connection to the proximal connector 4.

The electrodes 17 and 21 or 24 and 26 may be used as bipolar pairs, commonly referred to as a "tip-to-ring" configuration, or individually in a unipolar configuration with the device housing 11 serving as the indifferent electrode, commonly referred to as the "can" or "case" electrode. The device housing 11 may also serve as a subcutaneous defibrillation electrode in combination with one or more of the defibrillation coil electrodes 8, 20 or 23 for defibrillation of the atria or ventricles. It is recognized that alternate lead systems may be substituted for the three lead system illustrated in FIG. 1. While a particular multi-chamber ICD and lead system is illustrated in FIG. 1, methodologies included in the present invention may be adapted for use with other dual chamber, or multichamber ICD systems involving multiple electrodes for pacing/sensing and/or defibrillation within the heart or external to the heart such as epicardial or subcutaneous placements. The implementation may also include a device that does not employ pacing leads as described above to detect and treat arrhythmias. For example, a device implanted subcutaneously or sub-muscularly in a position over the heart such as an axillary location could use non-intracardiac lead based methods of electrical sensing to detect and deliver therapy.

Figure 2:
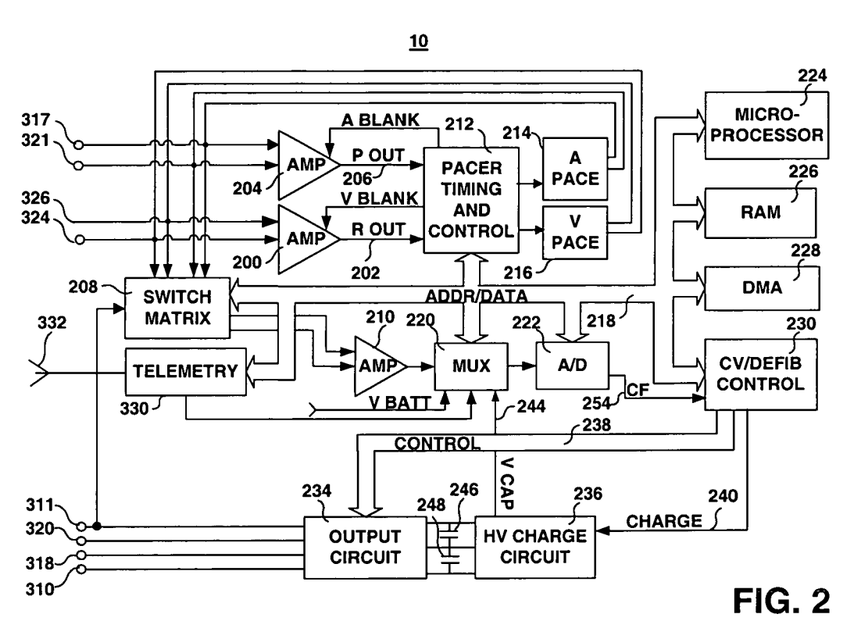
FIG. 2 is a functional block diagram of the implantable medical device shown in FIG. 1.

FIG. 2 is a functional block diagram of the implantable medical device shown in FIG. 1. This diagram should be taken as exemplary of the type of device with which the invention may be embodied and not as limiting, as it is believed that the invention may usefully be practiced in a wide variety of device implementations, which may or may not include any of the cardiac stimulation therapies described above, i.e., bradycardia pacing, anti-tachycardia pacing, high-frequency pulse bursts, cardioversion shocks, defibrillation shocks, or other cardiac stimulation therapies. The disclosed embodiment shown in FIG. 2 is a microprocessor-controlled device, but the methods of the present invention may also be practiced with devices employing dedicated digital circuitry for controlling some device functions.

With regard to the electrode system illustrated in FIG. 1, the ICD 10 is provided with a number of connection terminals for achieving electrical connection to the cardiac leads 6, 15, and 16 and their respective electrodes. The connection terminal 311 provides electrical connection to the housing 11 for use as the indifferent electrode during unipolar stimulation or sensing. The connection terminals 320, 310, and 318 provide electrical connection to coil electrodes 20, 8 and 23 respectively. Each of these connection terminals 311, 320, 310, and 318 are coupled to the high voltage output circuit 234 to facilitate the delivery of high energy shocking pulses to the heart using one or more of the coil electrodes 8, 20, and 23 and optionally the housing 11. In accordance with the present invention, and as will be described in greater detail below, a shock vector may be selected from the available coil electrodes based on the status of both the atrial and ventricular rhythms.

The connection terminals 317 and 321 provide electrical connection to tip electrode 17 and ring electrode 21 positioned in the right atrium. The connection terminals 317 and 321 are further coupled to an atrial sense amplifier 204 for sensing atrial signals such as P-waves. The connection terminals 326 and 324 provide electrical connection to tip electrode 26 and the ring electrode 24 positioned in the right ventricle. The connection terminals 326 and 324 are further coupled to a ventricular sense amplifier 200 for sensing ventricular signals.

The atrial sense amplifier 204 and the ventricular sense amplifier 200 preferably take the form of automatic gain controlled amplifiers with adjustable sensing thresholds. The general operation of the ventricular sense amplifier 200 and the atrial sense amplifier 204 may correspond to that disclosed in U.S. Pat. No. 5,117,824, by Keimel, et al., incorporated herein by reference in its entirety. Whenever a signal received by atrial sense amplifier 204 exceeds an atrial sensing threshold, a signal is generated on the P-out signal line 206. Whenever a signal received by the ventricular sense amplifier 200 exceeds a ventricular sensing threshold, a signal is generated on the R-out signal line 202.

Switch matrix 208 is used to select which of the available electrodes are coupled to a wide band amplifier 210 for use in digital signal analysis. Selection of the electrodes is controlled by the microprocessor 224 via data/address bus 218. The selected electrode configuration may be varied as desired for the various sensing, pacing, cardioversion and defibrillation functions of the ICD 10. Signals from the electrodes selected for coupling to bandpass amplifier 210 are provided to multiplexer 220, and thereafter converted to multi-bit digital signals by A/D converter 222, for storage in random access memory 226 under control of direct memory access circuit 228. Microprocessor 224 may employ digital signal analysis techniques to characterize the digitized signals stored in random access memory 226 to recognize and classify the patient's heart rhythm employing any of the numerous signal processing methods known in the art.

The telemetry circuit 330 receives downlink telemetry from and sends uplink telemetry to an external programmer, as is conventional in implantable anti-arrhythmia devices, by means of an antenna 332. Received telemetry is provided to microprocessor 224 via multiplexer 220. Data to be uplinked to the programmer and control signals for the telemetry circuit 330 are provided by microprocessor 224 via address/data bus 218. Data to be uplinked may include a record of detected and classified arrhythmia episodes as is customary in modern ICDs. Numerous types of telemetry systems known for use in implantable devices may be used.

The remainder of circuitry illustrated in FIG. 2 is dedicated to the provision of cardiac pacing, cardioversion and defibrillation therapies and, for the purposes of the present invention, may correspond to circuitry known in the prior art. In the exemplary embodiment shown in FIG. 2, the pacer timing and control circuitry 212 includes programmable digital counters which control the basic time intervals associated with various single, dual or multi-chamber pacing modes or anti-tachycardia pacing therapies delivered in the atria or ventricles. Pacer circuitry 212 also determines the amplitude of the cardiac pacing pulses under the control of microprocessor 224.

During pacing, escape interval counters within pacer timing and control circuitry 212 are reset upon sensing of R-waves or P-waves as indicated by signals on lines 202 and 206, respectively. In accordance with the selected mode of pacing, pacing pulses are generated by atrial pacer output circuit 214 and ventricular pacer output circuit 216. The pacer output circuits 214 and 216 are coupled to the desired electrodes for pacing via switch matrix 208. The escape interval counters are reset upon generation of pacing pulses, and thereby control the basic timing of cardiac pacing functions, including anti-tachycardia pacing.

The durations of the escape intervals are determined by microprocessor 224 via data/address bus 218. The value of the count present in the escape interval counters when reset by sensed R-waves or P-waves can be used to measure R-R intervals, P-P intervals, P-R intervals, and R-P intervals, which measures are stored in memory 226 and to diagnose the occurrence of a variety of arrhythmias.

Microprocessor 224 operates as an interrupt driven device and is responsive to interrupts from pacer timing and control circuitry 212 corresponding to the occurrences of sensed P-waves and R-waves and corresponding to the generation of cardiac pacing pulses. Any necessary mathematical calculations to be performed by microprocessor 224 and any updating of the values or intervals controlled by pacer timing/control circuitry 212 take place following such interrupts. A portion of the random access memory 226 may be configured as a number of recirculating buffers capable of holding a series of measured intervals, which may be analyzed in response to a pace or sense interrupt by microprocessor 224 for diagnosing an arrhythmia. Any of the various arrhythmia detection methodologies known to the art may be employed for detecting ventricular arrhythmias. Methods for detecting and discriminating atrial arrhythmias will be described in conjunction with FIG. 3.

In response to the detection of atrial or ventricular tachycardia, an anti-tachycardia pacing therapy may be delivered if desired by loading a regimen from microcontroller 224 into the pacer timing and control circuitry 212 according to the type of tachycardia detected. Alternatively, circuitry for controlling the timing and generation of anti-tachycardia pacing pulses as generally described in U.S. Pat. No. 4,577,633 issued to Berkovits et al., U.S. Pat. No. 4,880,005 issued to Pless et al., U.S. Pat. No. 4,726,380 issued to Vollmann et al., and U.S. Pat. No. 4,587,970 issued to Holley et al, all of which patents are incorporated herein by reference in their entireties, may be used.

In the event that higher voltage cardioversion or defibrillation shock pulses are required, microprocessor 224 activates the cardioversion and defibrillation control circuitry 230 to initiate charging of the high voltage capacitors 246 and 248 via charging circuit 236 under the control of high voltage charging control line 240. The voltage on the high voltage capacitors 246 and 248 is monitored via a voltage capacitor (VCAP) line 244, which is passed through the multiplexer 220. When the voltage reaches a predetermined value set by microprocessor 224, a logic signal is generated on the capacitor full (CF) line 254, terminating charging. Thereafter, timing of the delivery of the defibrillation or cardioversion pulse is controlled by pacer timing and control circuitry 212.

One embodiment of an appropriate system for delivery and synchronization of ventricular cardioversion and defibrillation pulses and for controlling the timing function related to them is generally disclosed in commonly assigned U.S. Pat. No. 5,188,105 to Keimel, incorporated herein by reference in its entirety. If atrial defibrillation capabilities are included in the device, appropriate systems for delivery and synchronization of atrial cardioversion and defibrillation pulses and for controlling the timing function related to them may be found in U.S. Pat. No. 4,316,472 issued to Mirowski et al., U.S. Pat. No. 5,411,524 issued to Mehra, or U.S. Pat. No. 6,091,988 issued to Warman, all of which patents are incorporated herein by reference in their entireties. Any known ventricular cardioversion or defibrillation pulse control circuitry may be usable in conjunction with the present invention. For example, circuitry controlling the timing and generation of cardioversion and defibrillation pulses as disclosed in U.S. Pat. No. 4,384,585, issued to Zipes, U.S. Pat. No. 4,949,719, issued to Pless et al., and in U.S. Pat. No. 4,375,817, issued to Engle et al., all incorporated herein by reference in their entireties may be used in a device employing with the present invention.

In the illustrated device, delivery of cardioversion or defibrillation pulses is accomplished by output circuit 234, under control of control circuitry 230 via control bus 238. Output circuit 234 determines the shock pulse waveform, e.g. whether a monophasic, biphasic or multiphasic pulse is delivered, whether the housing 311 serves as cathode or anode, which electrodes are involved in delivery of the pulse, and the pulse shape and tilt. Examples of high-voltage cardioversion or defibrillation output circuitry are generally disclosed in U.S. Pat. No. 4,727,877 issued to Kallok, and U.S. Pat. No. 5,163,427 issued to Keimel, both incorporated herein by reference in their entirety.

In modern implantable cardioverter defibrillators, the particular therapies are programmed into the device ahead of time by the physician, and a menu of therapies is typically provided. For example, on initial detection of tachycardia, an anti-tachycardia pacing therapy may be selected. On redetection of tachycardia, a more aggressive anti-tachycardia pacing therapy may be scheduled. If repeated attempts at anti-tachycardia pacing therapies fail, a higher-level cardioversion pulse therapy may be selected thereafter. As in the case of currently available ICDs, and as discussed in the above-cited references, it is envisioned that the amplitude of the defibrillation shock may be incremented in response to failure of an initial shock or shocks to terminate fibrillation. Prior art patents illustrating such pre-set therapy menus of anti-tachycardia therapies include the above-cited U.S. Pat. No. 4,726,380 issued to Vollmann et al., above cited U.S. Pat. No. 4,587,970 issued to Holley et al., and U.S. Pat. No. 4,830,006 issued to Haluska, incorporated herein by reference in their entirety.

Figure 3:
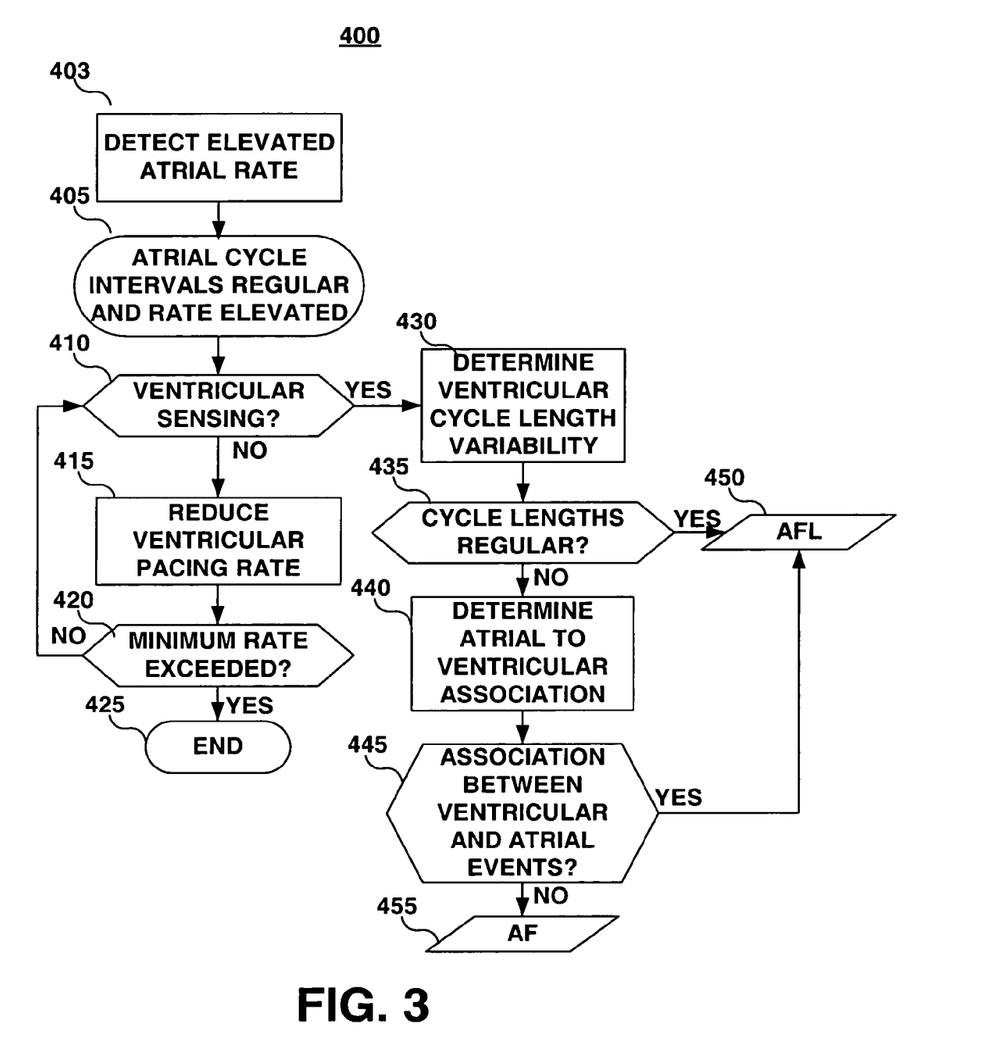
FIG. 3 is a flow diagram providing an overview of a method for detecting and classifying an atrial arrhythmia according to the present invention.

FIG. 3 is a flow diagram providing an overview of a method for detecting and classifying an atrial arrhythmia according to the present invention. The algorithm shown in FIG. 3 for discriminating atrial flutter from atrial fibrillation is initiated at step 405 when an elevated atrial rate is sensed which satisfies atrial arrhythmia detection interval criteria, step 403, and the atrial rate is regular. If a high rate is detected but the rate is irregular, a detection of atrial fibrillation is generally made without requiring additional evaluation of the ventricular rhythm. The atrial flutter/atrial fibrillation discrimination method 400 is therefore employed when atrial cycle length information does not clearly indicate atrial fibrillation.

The atrial rate may be determined by measuring the intervals between sensed atrial events, such as P-P intervals measured between sensed P-waves detected by atrial sensing circuitry receiving EGM signals as input. However, an atrial rate may alternatively be derived from other cardiac-related signals from which electrical or mechanical events associated with atrial depolarizations may be sensed and used in determining the rate of such events. Multiple cardiac event detection methods have been described or are in practice.

Typically, a programmable number of atrial event intervals shorter than a specified atrial arrhythmia detection interval must be sensed in order to begin detecting an atrial arrhythmia. An atrial flutter detection interval and number of intervals to detect atrial flutter, and an atrial fibrillation detection interval and number of intervals to detect atrial fibrillation may be uniquely defined, as is known in prior art. Once such atrial rate-related criteria are satisfied, the regularity of the atrial rhythm may be examined. The regularity may be determined based on the difference between maximum and minimum atrial event cycle lengths out of a given number of measured atrial cycle lengths. If this difference is less than a specified amount, for example less than 25% of the median atrial cycle length, the rate is considered regular. Other methods known in the art for measuring cycle length regularity may alternatively be employed.

In some patients, atrial flutter and atrial fibrillation detection interval criteria may be defined which have an overlapping detection interval zone. Atrial cycle length regularity may be examined if a detected atrial rate falls within the overlap zone. However, the atrial fibrillation/atrial flutter discrimination method shown in FIG. 3 may also be utilized whenever a fast atrial rate is detected, i.e., the sensed rate is faster than the slowest arrhythmia detection rate, not exclusively during rate detections falling into an atrial flutter/atrial fibrillation overlap zone.

Once a high atrial rate is detected, and the atrial cycle length information is determined to be ambiguous in distinguishing atrial flutter from atrial fibrillation, i.e., atrial cycle length regularity criteria are met, method 400 proceeds to step 410. At decision step 410, a determination is made as to whether ventricular sensing is present. In accordance with the present invention, the intrinsic ventricular rhythm will be evaluated to distinguish atrial flutter from atrial fibrillation based on the effect of the atrial arrhythmia on the ventricular rhythm. A minimum number of sensed ventricular events may be required in order to evaluate the ventricular rhythm. For example, on the order of 6 to 10 consecutively sensed ventricular cycles, without intervening ventricular pacing pulses, may be required at step 410 before proceeding to step 430 for evaluating the ventricular rhythm. Ventricular events may be R-waves sensed by ventricular sensing circuitry receiving an EGM signal as input but may alternatively be other electrical or mechanical events sensed from a cardiac-related signal and associated with ventricular depolarizations.

If ventricular pacing is occurring at step 410, the ventricular pacing rate is reduced at step 415 in an attempt to allow sensing of intrinsic ventricular events. The ventricular pacing rate is reduced in stepwise decrements until ventricular sensing is present, as determined at decision step 410, or until a predetermined minimum ventricular pacing rate is reached, as determined at decision step 420. If ventricular intrinsic event sensing is still not occurring after reaching a specified minimum ventricular pacing rate, e.g. a minimum rate of 50 beats per minute, method 400 is terminated at step 425. The absence of sensed intrinsic ventricular activity precludes evaluation of the intrinsic ventricular rhythm for use in discriminating atrial arrhythmias.

Reduction of the ventricular pacing rate at step 415 is preferably performed only when the patient is not dependent on ventricular pacing for maintaining a minimal base rate. If a patient is known to be pacing dependent, method 400 may not be enabled to operate. In alternative embodiments, an evaluation of the frequency of ventricular pacing during a recent time interval may be used to determine the dependency on pacing. If ventricular pacing is occurring a majority of the time, method 400 may be temporarily disabled.

If ventricular sensing is present for a specified period of time or number of cardiac cycles without intervening pacing pulses, as determined at decision step 410, method 400 proceeds to step 430 to determine the intrinsic ventricular cycle length variability, e.g., the R-R interval variability. R-R interval variability may be measured as the difference between the maximum and minimum R-R intervals occurring during a specified number of consecutively sensed R-R intervals.

At decision step 435, the ventricular event interval variability is compared to regularity criteria. For example, the difference between the maximum and minimum R-R intervals determined as a measure of cycle length variability at step 430 may be compared to some maximum value, a percentage of the average or median R-R interval or other regularity threshold. If the difference between the maximum and minimum R-R interval is less than the regularity threshold, the intrinsic ventricular rate is considered regular. Other methods known in the art for measuring ventricular cycle length variability may be substituted.

If the ventricular cycle lengths are determined to be regular during the elevated atrial rate (step 435), the atrial rhythm is classified as atrial flutter at step 450. If the ventricular cycle lengths are not determined to be regular at step 435, the relation between sensed ventricular events and sensed atrial events is evaluated at step 440 to determine if the sensed ventricular events, such as R-waves, are associated with sensed atrial events, such as P-waves. For example, the association of sensed R-waves to sensed P-waves may be determined by comparing measured R-R intervals to measured P-P intervals. In particular, if measured R-R intervals are approximately equal to measured P-P intervals or a whole multiple of measured P-P intervals, atrial flutter is indicated as shown by step 450. During atrial flutter, P-waves can be conducted to the ventricle with every, every other or every third heart beat such that atrial events are sensed at a 1:1, 2:1 or 3:1 ratio to ventricular events.

Alternatively, the association of ventricular and atrial sensed events may be determined according to the time interval between a sensed atrial event and a sensed ventricular event. For example, if measured P-R intervals fall within a specified range, which includes the expected conduction time between the atria and the ventricles, the R-wave is likely to be a depolarization conducted from the atria. If sensed R-waves are determined to be associated with sensed P-waves and the ratio of P-waves to R-waves is regular, e.g., a 1:1, 2:1, or 3:1 ratio, atrial flutter is indicated as shown by step 450.

Additionally, the association of ventricular to atrial events may be examined to recognize a pattern of Wenckebach conduction. In this case, 1:1 conduction occurs for a number of cardiac cycles followed by a missed conduction. The P-P intervals and R-R intervals are regular and approximately equal during the 1:1 conduction period followed by a longer R-R interval that is extended by a time interval corresponding to the non-conducted atrial cycle length. For example, a repetitive pattern of a 3:4 ratio of ventricular to atrial sensed events may occur wherein 1:1 conduction occurs for the first three atrial events but the fourth is not conducted. Two R-R intervals approximately equal to the corresponding P-P intervals will be measured followed by a third, long R-R interval approximately equal to two P-P intervals.

If the ventricular rhythm is independent of the atrial rhythm, i.e., ventricular events are determined to be disassociated from sensed atrial events at step 445 because R-waves do not occur at a regular ratio to or a regular interval following sensed P-waves or because R-R cycle lengths are unrelated to P-P cycle lengths, atrial fibrillation is detected as indicated at step 455.

The atrial arrhythmia episode information may then be stored along with the atrial flutter or atrial fibrillation classification made at step 450 or 455 such that it is available at later device interrogation sessions for monitoring and diagnostic purposes. The atrial arrhythmia classification made at step 450 or 455 may additionally or alternatively be used in selecting and delivering an appropriate atrial arrhythmia therapy, which may be a cardiac stimulation therapy or an alternative therapy such as drug delivery. If the atrial flutter/atrial fibrillation discrimination method 400 cannot be performed or is inconclusive due to insufficient sensing of the intrinsic ventricular activity, a selected cardiac stimulation therapy may be delivered according to programmed atrial flutter therapies such that less aggressive cardiac stimulation therapies are attempted upon detection of the high atrial rate. Stored atrial arrhythmia episode data and atrial flutter or atrial fibrillation classification can also be used by a clinician or researcher in evaluating the effectiveness of or regulating atrial arrhythmia therapies.

Thus, a system and method have been described for discriminating atrial arrhythmias based on sensing and evaluating the intrinsic ventricular rhythm. Accurate discrimination of atrial flutter from atrial fibrillation is beneficial in selecting appropriate therapies and in monitoring purposes, particularly in patients that experience atrial fibrillation having regular cycle lengths. While the present invention has been described according to specific embodiments presented herein, these embodiments are intended to be exemplary, not limiting, with regard to the following claims.

We claim:

1. An implantable medical device, comprising:
   means for sensing a heart rate indicative of an arrhythmia associated with a first portion of a heart;
   means for determining regularity of the sensed heart rate;
   means for determining an event interval variability associated with a second portion of the heart;
   means for classifying the arrhythmia in response to the determined event interval variability;
   means for determining whether a therapy is being delivered to the second portion of the heart;
   means for varying the therapy prior to determining the event interval variability in response to the therapy being delivered; and
   means for determining whether sensing is present in the second portion of the heart, and wherein the means for varying the therapy includes reducing the therapy until one of determining sensing is present and the therapy being delivered at a predetermined minimum rate, wherein the means for determining whether sensing is present determines the frequency of the therapy during a predetermined time interval and disables the means for determining an event interval variability and the means for classifying the arrhythmia.

2. An implantable medical device, comprising:
means for sensing a heart rate indicative of an arrhythmia associated with a first portion of a heart;
means for determining regularity of the sensed heart rate;
means for detemining an event interval variability associated with a second portion of the heart;
means for classifying the arrhythmia in response to the determined event interval variability; and
means for determining R-R intervals, wherein the means for determining the event interval variability determines a difference between maximum R-R intervals and minimum R-R intervals occurring during a predetermined number of consecutive R-R intervals, wherein the means for determining the event interval variability determines whether the difference between maximum R-R intervals and minimum R-R intervals is less than a regularity threshold, and wherein the means for classifying the arrhythmia determines the arrhythmia is a first arrhythmia in response to the difference between maximum R-R intervals and minimum R-R intervals being less than the regularity threshold.

3. The device of claim 2, wherein the means for determining the event interval variability determines whether events associated with the second portion of the heart are associated with events associated with the first portion of the heart, wherein the means for classifying the arrhythmia determines the arrhythmia is the first arrhythmia in response to events associated with the second portion of the heart being associated with events associated with the first portion of the heart.

4. The device of claim 3, wherein the arrhythmia is classified as a second arrhythmia different from the first arrhythmia in response to events associated with the second portion of the heart not being associated with events associated with the first portion of the heart.

5. The device of claim 4, wherein the arrhythmia is classified as the first arrhythmia in response to events associated with the second portion of the heart being associated with events associated with the first portion of the heart such that intervals of events associated with the second portion of the heart are approximately equal an integer multiple of intervals of events associated with the first portion of the heart.

6. A method of detecting and classifying an arrhythmia, comprising:
sensing a heart rate indicative of an arrhythmia associated with a first portion of a heart;
determining regularity of the sensed heart rate;
determining an event interval variability associated with a second portion of the heart;
classifying the arrhythmia in response to the determined event interval variability;
determining whether a therapy is being delivered to the second portion of the heart;
varying the therapy prior to determining the event interval variability in response to the therapy being delivered; and
determining whether sensing is present in the second portion of the heart, wherein varying the therapy includes reducing the therapy until one of determining sensing is present and the therapy being delivered at a predetermined minimum rate, and wherein determining whether sensing is present includes determining the frequency of the therapy during a predetermined time interval and disabling the method in response to the determined frequency having a predetermined value.

7. A method of detecting and classifying an arrhythmia, comprising:
sensing a heart rate indicative of an arrhythmia associated with a first portion of a heart;
determining regularity of the sensed heart rate;
determining an event interval variability associated with a second portion of the heart;
classifying the arrhythmia in response to the determined event interval variability;
sensing R-R intervals, wherein determining the event interval variability includes determining a difference between maximum R-R intervals and minimum R-R intervals occurring during a predetermined number of consecutively sensed R-R intervals; and
determining whether the difference between maximum R-R intervals and minimum R-R intervals is less than a regularity threshold, wherein the arrhythmia is classified as a first arrhythmia in response to the difference between maximum R-R intervals and minimum R-R intervals being less than the regularity threshold.

8. The method of claim 7, further comprising determining whether events associated with the second portion of the heart are associated with events associated with the first portion of the heart, wherein the arrhythmia is classified as the first arrhythmia in response to events associated with the second portion of the heart being associated with events associated with the first portion of the heart.

9. The method of claim 8, wherein the arrhythmia is classified as a second arrhythmia different from the first arrhythmia in response to events associated with the second portion of the heart not being associated with events associated with the first portion of the heart.

10. The method of claim 9, wherein the arrhythmia is classified as the first arrhythmia in response to events associated with the second portion of the heart being associated with events associated with the first portion of the heart such that intervals of events associated with the second portion of the heart are approximately equal an integer multiple of intervals of events associated with the first portion of the heart.

11. An implantable medical device, comprising:
means for sensing a heart rate indicative of an arrhythmia associated with a first portion of a heart;
means for determining regularity of the sensed heart rate;
means for determining an event interval variability associated with a second portion of the heart;
means for classifying the arrhythmia in response to the determined event interval variability;
means for determining whether a therapy is being delivered to the second portion of the heart;
means for varying the therapy prior to determining the event interval variability in response to the therapy being delivered; and
means for determining whether sensing is present in the second portion of the heart, wherein the means for varying the therapy includes reducing the therapy until one of determining sensing is present and the therapy being delivered at a predetermined minimum rate, and the means for determining whether sensing is present determines the frequency of the therapy during a predetermined time interval and disables the means for determining an event interval variability and the means for classifying the arrhythmia.

12. The device of claim 11, further comprising means for determining R-R intervals, wherein the means for determining the event interval variability determines a difference between maximum R-R intervals and minimum R-R intervals occurring during a predetermined number of consecutive R-R intervals.

13. The device of claim 12, wherein the means for determining the event interval variability determines whether the difference between maximum R-R intervals and minimum R-R intervals is less than a regularity threshold, wherein the means for classifying the arrhythmia determines the arrhythmia is a first arrhythmia in response to the difference between maximum R-R intervals and minimum R-R intervals being less than the regularity threshold.

14. The device of claim 13, wherein the means for determining the event interval variability determines whether events associated with the second portion of the heart are associated with events associated with the first portion of the heart, wherein the means for classifying the arrhythmia determines the arrhythmia is the first arrhythmia in response to events associated with the second portion of the heart being associated with events associated with the first portion of the head.

15. The device of claim 14, wherein the arrhythmia is classified as a second arrhythmia different from the first arrhythmia in response to events associated with the second portion of the heart not being associated with events associated with the first portion of the heart.

16. The device of claim 15, wherein the arrhythmia is classified as the first arrhythmia in response to events associated with the second portion of the heart being associated with events associated with the first portion of the heart such that intervals of events associated with the second portion of the heart are approximately equal an integer multiple of intervals of events associated with the first portion of the heart.

* * * * *